United States Patent [19]
Pettibone et al.

[11] Patent Number: 5,198,463
[45] Date of Patent: Mar. 30, 1993

[54] OXYTOCIN ANTAGONISTS

[75] Inventors: Douglas J. Pettibone, Chalfont, Pa.; Gino M. Salituro, Fanwood, N.J.

[73] Assignee: Merck & Co., Inc., Rahway, N.J.

[21] Appl. No.: 860,335

[22] Filed: Mar. 30, 1992

[51] Int. Cl.[5] .......................................... A61K 31/335
[52] U.S. Cl. ..................... 514/450; 514/906; 514/935
[58] Field of Search ..................... 514/450, 906, 935

[56] References Cited

U.S. PATENT DOCUMENTS 5,089,487  2/1992  Frobel et al. .................. 514/150

OTHER PUBLICATIONS

Suzuki et al., Phytochemistry, 30(6), 2906-98 (1991).
Nishida et al. (I), J. Antibiotics, 44(2), 144-51 (1991).
Nishida et al. (II), J. Antibiotics, 44(2), 152-59 (1991).
Sassa, et al., Tetrahedron Letters, 45, 3941-942 (1974).

Primary Examiner—Frederick E. Waddell
Assistant Examiner—Kimberly R. Jordan
Attorney, Agent, or Firm—Frank P. Grassler; Alice O. Robertson; Charles M. Caruso

[57] ABSTRACT

A method for inhibiting oxytocin activity by administering an oxytocin inhibiting amount of a penicillide compound having the formula

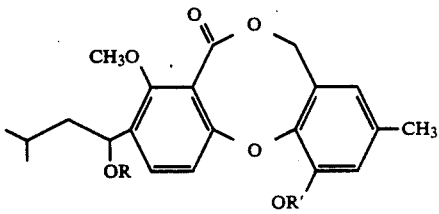

and compositions for such use are described.

6 Claims, No Drawings

OXYTOCIN ANTAGONISTS

Oxytocin has the property of stimulating the frequency and force of contractile activity in uterine smooth muscle. It promotes the contraction of myoepithelium which forces milk from alveolar channels into large sinuses making it more easily available to suckling infants. It also has a relaxing effect on vascular smooth muscle. The first of the foregoing properties is sometimes associated with an undesirable effect, namely that of premature labor or threatened abortion. Nonsteroidal anti-inflammatory agents and β-adrenoceptor agonists have been used to inhibit premature labor and/or threatened abortion; however, these treatments are not selective and are accompanied by adverse side effects. In addition, peptidyl oxytocin antagonists have recently been shown to be effective to inhibit preterm labor. It would be desirable to have a non-steroidal, non-peptidyl, preferably small organic compound which has the property of inhibiting oxytocin activity.

Penicillide, a metabolit isolated from the mycelial extracts of Penicillium sp., having the structure:

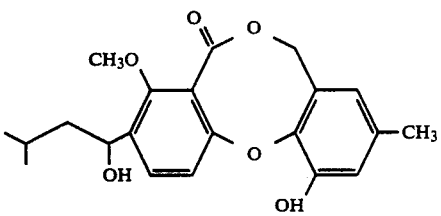

and the monoethyl ether thereof are reported by T. Sassa et al. to be a growth inhibitor which markedly inhibits the growth of Chinese cabbage seedlings. No other use is suggested.

Purpactins, produced by *Penicillium purpurogenum*, are reported to be inhibitors of acyl-CoA: cholesterol acyltransferase (ACAT). Purpactins inhibit ACAT activity in vitro and in living cells.

According to the present invention, it has been discovered that penicillide, a metabolite of a Penicillium species, and certain derivatives of penicillide have the property of antagonizing oxytocin activity. Thus, it is useful where needed for relaxing smooth muscle or for inhibiting and reducing contractile activity, and is adaptable to being used in a composition for treating premature labor.

Penicillide and derivatives thereof, hereinafter "a penicillide compound" may be represented by the following formula:

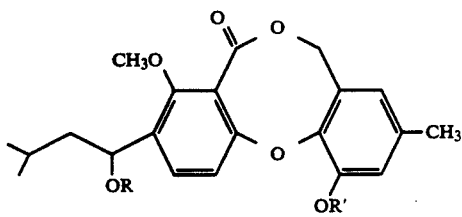

In the above and succeeding formulas, R is H or COCH₃ and R¹ is H, COCH₃, or CH₃.

When R and R¹ are both H, the compound, as previously noted, is a natural product identified in the literature as penicillide and may be represented by formula (IA):

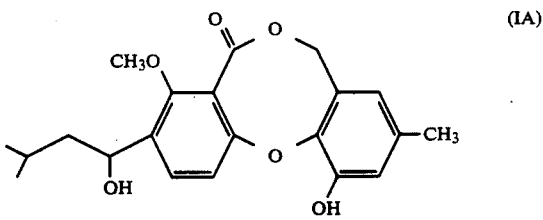

The compound is produced by the cultivation of a Penicillium genus as hereinafter described.

When R and R¹ are both COCH₃, the compound may be represented by formula (IB):

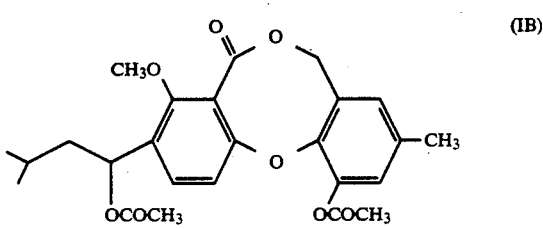

and may be obtained by acetylation of penicillide as hereinafter described or may be isolated as a minor component in the cultivation of Penicillium sp.

When R is COCH₃ and R¹ is H, the monoacetate compound may be represented by formula (IC):

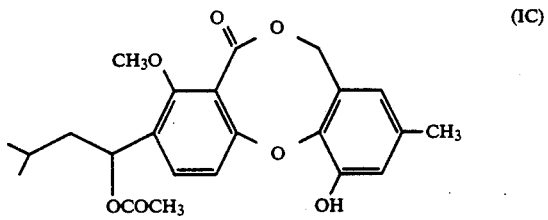

and is obtained by the controlled reduction of the diacetate as hereinafter described.

When R is COCH₃ and R¹ is CH₃, the compound may be represented by formula (ID):

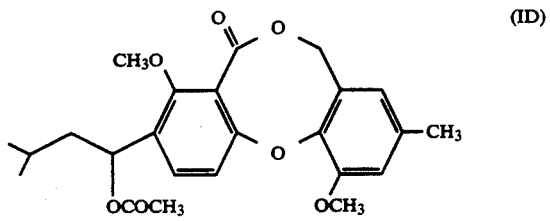

and is obtained by methylation of penicillide followed by acetylation as hereinafter described.

The spectral properties of the foregoing compounds are as follows:

Mass Spectra. Mass spectra were recorded on a Finnigan-MAT 212 mass spectrometer (electron impact, EI, 90eV). Exact mass measurements were performed at high resolution (HR-EI) using perfluorokerosene (PFK) as an internal standard. Trimethylsilyl (TMS) derivatives were prepared with a 1:1 mixture of bis(-trimethylsilyl) trifluoroacetamide (BSTFA)-pyridine at room temperature. The mass spectral data were as follows:

| Compound | Molecular formula | Calcd | Found |
|---|---|---|---|
| IA | $C_{21}H_{24}O_6 + (C_3H_8Si)_2$ | 516.2363 | 576.2395 |
| IB | $C_{25}H_{28}O_8$ | 456.1784 | 456.1787 |
| IC | $C_{23}H_{26}O_7$ | 414.1678 | 414.1670 |
| ID | $C_{24}H_{28}O_7$ | 428.1835 | 428.1832 |

NMR Spectra. The NMR shifts were recorded on a Varian XL-400 NMR spectrometer at 24° C. in $CDCl_3$ at 300 MHz.

The NMR spectral characteristics of Compound IA were as follows:

$^1$H NMR: 7.54 (d, J=8.5 Hz, 1H), 6.95 (d, J=2.0 Hz, 1H), 6.92 (d, J=8.5 Hz, 1H), 6.52 (br.s, 1H), 6.35 (d, J=2.0 Hz, 1H), 5.05 (br. m, 3H), 3.98 (s, 3H), 2.23 (s, 3H), 1.78 (m, 1H), 1.65 (m, 1H), 1.47 (m, 1H), 0.97 (d, J=7.1 Hz, 3H), 0.95 (d, J=6.9 Hz, 3H).

$^{13}$C NMR: 168.0, 154.3, 151.3, 147.5, 141.4, 136.8, 135.0, 131.0, 125.7, 120.6, 119.4, 117.8, 117.7, 69.2, 66.6, 62.6, 47.6, 25.0, 23.4, 22.7, 20.9.

The NMR spectral characteristics of Compound IB were as follows:

$^1$H NMR: 7.44 (d, J=8.6 Hz, 1H), 6.96 (d, J=8.6 Hz, 1H), 6.93 (d, J=1.6 Hz, 1H), 6.70 (d, J=1.6 Hz, 1H), 6.11 (dd, J=4.5 Hz, 9.1 Hz, 1H), 5.50 (d, J=14 Hz, 1H), 5.01 (d, J=14 Hz, 1H), 4.02 (s, 3H), 2.38 (s, 3H), 2.29 (s, 3H), 2.06 (s, 3H), 1.77 (m, 1H), 1.62 (m, 1H), 1.53 (m, 1H), 0.96 (d, J=6.0 Hz, 3H), 0.94 (d, J=6.0 Hz, 3H).

$^{13}$C NMR: 170.3, 169.8, 167.2, 154.6, 153.2, 147.4, 141.2, 136.1, 134.3, 130.8, 125.8, 120.8, 120.1, 117.8, 117.6, 69.0, 68.7, 62.7, 45.3, 24.9, 23.0, 22.1, 21.6, 21.1, 20.9.

The NMR spectral characteristics of Compound IC were as follows:

$^1$H NMR: 7.43 (d, J=8.5 Hz, 1H), 6.87 (d, J=8.5 Hz, 1H), 6.84 (d, J=1.7 Hz, 1H), 6.33 (d, J=1.7 Hz, 1H), 6.29 (br. s, 1H), 6.11 (dd, J=4.3 Hz, 9.2 Hz, 1H), 5.03 (br. m, 2H), 4.02 (s, 3H), 2.23(s, 3H), 2.06 (s, 3H), 1.75 (m, 1H), 1.63 (m, 1H), 1.47 (m, 1H), 0.94 (d, J=6.5 Hz, 3H), 0.94 (d, J=6.5 Hz, 3H).

$^{13}$C NMR: 170.3, 167.2, 154.6, 151.5, 147.3, 141.2, 135.1, 134.2, 130.7, 125.8, 120.8, 120.0, 117.8, 117.6, 69.0, 68.7, 62.7, 45.3, 24.9, 23.1, 21.9, 21.1, 20.9.

The NMR spectral characteristics of Compound ID were as follows:

$^1$H NMR: 7.42 (d, J=8.5 Hz, 1H), 6.95 (d, J=8.5 Hz, 1H), 6.75 (d, J=1.5 Hz, 1H), 6.43 (d, J=1.5 Hz, 1H), 6.13 (dd, J=4.5 Hz, 8.3 Hz, 1H), 5.14 (d, J=14.5 Hz, 1H), 5.01 (d, J=14.5 Hz, 1H), 4.02 (s, 3H), 3.94 (s, 3H), 2.29 (s, 3H), 2.05 (s, 3H), 1.77 (m, 1H), 1.58 (m, 2H), 0.95 (d, J=6.0 Hz, 3H), 0.93 (d, J=6.0 Hz, 3H).

$^{13}$C NMR: 170.3, 167.2, 154.7, 152.5, 151.3, 143.2, 134.7, 133.3, 130.7, 126.9, 121.0, 119.7, 117.9, 114.5, 69.0, 68.7, 62.7, 56.4, 45.3, 24.9, 23.1, 21.9, 21.1, 20.9.

The oxytocin antagonist activity may be demonstrated in its ability to inhibit the binding of [$^3$H]-oxytocin in the rat uterus. An assay by which this may be demonstrated is similar to that described by Fuchs et al in J. Clin. Endocrin. Metab. 60: 37–41, 1985.

The assay may be carried out by first (1) preparing assay tubes containing either 50 microliters of cold oxytocin or 50 microliters of test drug and bring the contents of the tubes to 150 microliters with a buffer solution of 50 mM TRIS.HCl, 5 mM $MgCl_2$ and 0.1% bovine serum albumin (BSA), pH 7.4 (2) adding to each tube 50 microliters of 6 nM $^3$H-oxytocin, (3) adding 100 microliters of a tissue suspension of a homogenized uterus from estrogen-treated adult rats (prepared as subsequently described), (4) vortexing the tubes and (5) incubating for sixty minutes at room temperature.

The contents of the tubes are then aspirated onto the filtermats of a Skatron cell harvester which has been prepared previously by soaking in the above described buffer solution and then washing with a wash buffer (pH 8.0) of 10 mM TRIS.HCl, 5 mM $MgCl_2$. The filtermats bearing the tissue are then placed onto a Skatron template and the filters punched into vials. Two (2) milliters of scintillation cocktail is added to each vial and shaken for 30 minutes to count the radioactivity bound to the filters.

The specific binding at equilibrium (incubating 60 minutes at room temperature), represents about 90 percent of the total binding.

A compound having an $IC_{50}$ of about 70 $\mu$M or less is of considerable interest as an oxytocin inhibitor. The compounds of the present invention show promise as oxytocin inhibitors, being active at concentrations in the neighborhood of 5 to 70 $\mu$M.

The process of the present invention of inhibiting oxytocin induced contractions such as uterine contractions of premature labor may be carried out by administering a therapeutic dose of a penicillide compound in a composition comprising the same. In general, the dose may be that sufficient to provide between about 10 milligrams to about 100 milligrams per kilogram of body weight per day while considering the patients' health, weight, age and other factors which influence drug response. The drug may be administered orally, parenterally or by intranasal application. When injection is the mode of administration I.V. is preferred. Application by drops and sprays also may be used. Buccal lozenges may be employed utilizing oral mucosa. The composition may be modified to deliver an amount comparable to that supplied by parenteral injection. Parenteral injection, however, is preferred.

Compositions of the penicillide compound is thus preferably prepared as liquid compositions containing from about .1 to 10 mg/ml. Such compositions also may be prepared from concentrate compositions which may contain about 90 percent compound and which are diluted prior to use.

The penicillide compounds useful in the methods and therapeutic compositions of the present invention may be obtained in the manner hereinafter described. If the pencillide compound is penicillide itself, it is obtained by fermentation, preferably by cultivation of *Taloromyces flavus* (*Penicillium wortmanni*) ATCC 74110 first in a seed medium and then in a nutrient production medium at pH between 5 and 8.1 in the temperature range of 20° to 28° C., preferably with agitation for at least several days, and then followed by isolation. If the penicillide compound is an acetate or acetate methyl ether, it is obtained by acetylation of penicillide or penicillide methyl ether, and if appropriate, followed by reduction using conventional chemical methods.

The microrganism, *Taloromyces flavus* (*Penicillium wortmanni*), employed in the present production of penicillides has been deposited under the Budapest Treaty in the Culture Collection of the American Type Culture Collection at 12301 Parklawn Drive, Rockville, Md. 20852, and registered as ATCC 74110.

The colonial and morphological description of *Talaromyces flavus*, MF 973, ATCC 74110, are as follows:

Colonies on Czapek Yeast Extract Agar (1 g $K_2HPO_4$, 5 g yeast extract, 30 g sucrose, 10 ml Czapek concentrate, 15 g agar/L $dH_2O$) at 25° C. fast growing, attaining a diameter of 28-30 mm in seven days. Mycelium moderately deep to dense, velutinous to floccose; margins entire; mycelium hyaline at the margins, Picric Yellow to Pale Lemon Yellow; reverse Raw Sienna to Sayal Brown (capitalized color names are from Ridgway, R., 1912, Color Standards and Nomenclature, Washington, D.C.). On Blakeslee's Malt Extract Agar (20 g malt extract, 1 g peptone, 20 g glucose, 20 g agar/L $DH_2O$) colonies fast growing, attaining diameter of 40-42 mm in seven days. Mycelium moderately deep, floccose, conidiogenesis sparse but more abundant than on CYA, Pyrite Yellow to Olive Yellow; reverse Reed Yellow to deep Olive Buff. Gymnothecia bright yellow 300-500 μm in diameter, scattered on colony surface, globose to hemispherical, mature within two weeks. Asci subspherical $9.5-11 \times 8.5-9$ μm; ascospores spherical to subspherical spinose $3-3.5 \times 2.6-3.0$ μm. Conidiophores borne on aerial hyphae, stipes smooth-walled $25-60 \times 2.5$ μm bearing biverticilliate terminal penicilli. Metulae appressed $12-14 \times 2-2.2$ μm bearing one to four acerose phialides $9.5-11 \times 2.2$ μm. Condia subspherical to ellipsoidal $2.2-2.6 \times 2.2$ μm with walls smooth.

The following are representative preparations of the penicillide compounds useful in the present invention but are not to be construed as limiting:

PENICILLIDE (Compound IA)

A frozen vegetative mycelia of MF973 *Taloromyces flavus* ATCC 74110 was inoculated into 10 milliliters of seed medium having the following composition

| Component | g/L |
| --- | --- |
| Corn Steep Liquor | 5.0 |
| Tomato Paste | 40.0 |
| Oat flour | 10.0 |
| Cerelose | 10.0 |
| *Trace Elements | 10.0 ml |

| *Trace Elements | |
| --- | --- |
| $FeSO_4.7H_2O$ | 1.0 |
| $MnSO_4.4H_2O$ | 1.0 |
| $CuCl_2.2H_2O$ | 0.025 |
| $ZnSO_4.7H_2O$ | 0.2 |
| $CaCl_2.2H_2O$ | 0.1 |
| $H_3BO_3$ | 0.06 |
| $(NH_4)_6Mo_7O_{24}.4H_2O$ | 0.019 |
| Distilled $H_2O$ | 1.0 liter | and the resulting medium incubated with shaking at 220 RPM for 72 hours at 25° C. Then, ten milliliters of this culture was transferred to a flask containing 500 milliliters of the same seed medium and the flask was incubated with shaking at 200 RPM for 72 hours at 25° C. At the end of this period, the entire contents of the flask were transferred to 50 liters having the following contents

| Component | g/L |
| --- | --- |
| L-Asparagine | 1.0 |
| Edamine (type S)* | 2.5 |
| Primatone HS** | 2.5 |
| Yeast Extract | 5.0 |
| Malt Extract | 10.0 |
| Sucrose | 5.0 |
| $CaCO_3$ | 5.0 |
| P-2000 | 2.0 ml |
| pH = 7.2-7.4 | |

*Lactalbumin hydrolysate, Sheffield Products
**Meat hydrolysate, Sheffield Products of the production medium and fermentation carried out under the following conditions; air flow of 15 liters per minute, temperature of 25° C., an initial agitation rate of 400 RPM which was increased to 600 RPM at 65 hours and the cultivation then terminated at 98 hours. The production batch areas harvested for isolation of the secondary metabalite.

The whole broth was extracted by adding 48 liters of methanol to 45 liters of the whole broth and agitating the resulting mixture for 30 minutes, filtering the extract and washing the pad with methanol to obtain a total of 98 liters of filtered extract.

The filtered extract was pumped into a 2.5 liter column of SP 207 (10 cm $\times$ 27.5 cm; Mitsubishi Chemicals) which previously had been prepared by washing successively with 8 liters of each of methanol, acetone, methanol and 50 percent aqueous methanol. Thereafter, the column was washed with 8 liters of 70 percent methanol. The column was then eluted with 100 percent methanol and 450 milliliter fractions collected. Fractions containing greater than 90 percent penicillide were pooled. The pooled fractions amounting to 3.6 liters were concentrated to 250 milliliters of aqueous solution.

The concentrated aqueous solution was mixed with 400 milliliters of ethyl acetate and 200 milliliters of water to extract the product into the ethyl acetate. The aqueous phase was extracted a second time with 400 milliliters of ethyl acetate. The organic layers were pooled and dried over sodium sulfate. Thereafter the solvent was vaporized to obtain 14 grams of an oily residue.

A one-liter silica gel column (5.0 cm $\times$ 55 cm; 60-200 mesh) was packed in 5:1 hexanes:acetone and the oily residue which had been dissolved in 25 milliliters of methylene chloride and 25 milliliters of column solvent was placed on the column. The column was eluted with 5:1 hexanes: acetone at 40 ml/min. After a 1.5 liter forecut, 425 milliliter fractions were collected for 12 fractions, then, the eluting solvent was changed to 1:1 hexanes: acetone for 10 more fractions. The rich cuts (as determined by HPLC assay) were combined to obtain 7.5 grams of penicillide of 28% purity.

The product was purified further by a second silica gel column (5.0 $\times$ 55 cm; Kieselgel 60 (EM Industries); 230-400 mesh) packed in 3:1 hexanes: acetone. The pencillide was applied as a solution in 40 milliliters of methylene chloride and the column developed with 3:1 hexanes: acetone at 40 milliliters per minute. A total of 400 milliliters were collected. Fractions which contained pure penicillide (as determined by HPLC and TLC assays) were evaporated to obtain 1.6 grams of penicillide which had the spectral properties previously set forth.

PENCILLIDE DIACETATE

Compound IB 1.2 milligrams (3.2 μmol) of penicillide was dissolved in 250 microliters of methylene chloride and to the resulting clear solution was added first 50 microliters of acetic anhydride and then 50 microliters of pyridine. The mixture was stirred overnight at room temperature to obtain the penicillide diacetate product. The reaction mixture was then diluted with 2 milliliters of methylene dichloride and the methylene dichloride solution washed with two 2 milliliter portions of 1N hydrochloric acid and two 2 milliliter portions of saturated brine. The washed organic solution was dried over anhydrous sodium sulfate, the sodium sulfate then filtered and the filtrate subjected to reduced pressure to evaporate and to obtain the diacetate product as a light yellow oil. The latter was purified by reverse phase HPLC (PARTISIL 5 ODS-3 (adsorbent for chromatography); 55:45 acetonitrile: water, 1.5 mL/min; 40° C.; rt=26.5 min). The fractions containing the diacetate were combined and the solvent vaporized to obtain 1.3 milligrams of product.

PENICILLIDE MONOACETATE

Compound IC 8.2 milligrams (22 μmole) of penicillide was dissolved in 2 milliliters of methylene chloride, 500 microliters of acetic anhydride and 600 microliters of pyridine and the mixture was stirred overnight. At the end of this period, the mixture was diluted with 5 milliliters of methylene chloride. The methylene chloride solution was washed successively with 5 milliliters of water, two 5 milliliter portions of 1N hydrochloric acid, two 5 milliliter portions of 5 percent sodium bicarbonate solution, and 5 milliliters of saturated brine. The washed methylene chloride solution was dried over anhydrous sodium sulfate, then filtered to remove the sulfate and the solvent vaporized from the filtrate to obtain a residue. The residue was dissolved in 2 milliliters of dimethoxyethane and to the resulting solution was added 3.2 milligrams (85 μmole) of sodium borohydride. The mixture was stirred at room temperature for two hours. The solution was diluted with 10 milliliters of methylene chloride and washed with two 7 milliliter portions of water and 7 milliliters of saturated brine. The washed organic solution was dried over anhydrous sodium sulfate, and the solvent then vaporized from the dried solution to obtain a residue. The residue was dissolved in 250 microliters of acetonitrile and purified by reverse phase HPLC (LICHROSORB RP reverse phase resins from E. Merck) 18 0.94×25 cm 55:45 acetonitrile: water 4.0 mL/min; room temperature; rt=24 min) to obtain 8.1 milligrams of the desired penicillide monoacetate. The spectral properties of the compounds were as previously set forth.

MONOMETHYL PENICILLIDE ACETATE

Compound ID

A. Monomethyl ether. 1.6 milligrams (4.3 micromoles) of penicillide was dissolved in 500 microliters of ethyl ether and to it was added 500 microliters of a freshly prepared ethereal solution of diazomethane. The resulting solution was stirred for 36 hours at room temperature. At the end of this period the solvent was vaporized to obtain the methyl ether as residue which was dissolved in 30 microliters of tetrahydrofuran plus 30 microliters of acetonitrile. The product was purified by reverse phase HPLC (Whatman Partisil 5 ODS 55:45 acetonitrile:water 1.5 mL/min, 40° C.; rt=22 min). Fractions containing the methyl ether product were combined and the solvent vaporized to recover 1.4 milligrams of monomethyl ether.

B. Methyl penicillide acetate. 0.7 milligram (1.9 micromoles) of penicillide monomethyl ether was dissolved in 500 microliters of methylene chloride, 25 microliters of acetic anhydride and 40 microliters of pyridine, and the resulting mixture stirred overnight at room temperature. At the end of this period, the volatiles were vaporized under reduced pressure to recover a yellow oil as residue. The residue was dissolved in 25 microliters of tetrahydrofuran and 25 microliters of acetonitrile and placed on a reverse phase HPLC column (PARTISIL 5 ODS-3, 55:45 acetonitrile:water, 1.5 mL/min; 40° C.; rt=29.5 min) The fractions containing the product were combined and the solvent vaporized to recover as residue 0.6 milligram of the desired monomethyl penicillide acetate product. The product had the spectral characteristics previously described.

Compositions to be employed in the practice of the present invention comprises a penicillide compound in sterile physiologically acceptable media such as physiological saline. Such compositions may also contain other ingredients for purposes such as for aiding solubility or for preservation or the like, said ingredients being acceptable for intravenous administration. The compositions may be prepared as concentrate compositions which may be appropriately diluted to the appropriate treating composition immediately prior to administration. A therapeutic composition as a unitary dose form may contain form 2 μg to 1000 mg of penicillide compound and as concentrate composition may contain up to 10 grams of the active compound.

Parenteral compositions may be prepared employing a penicillide compound in a manner herinafter described.

PARENTERAL COMPOSITION

One liter of a parenteral composition comprising one of the preferred compounds or one of the foregoing compounds may be prepared from the following formulation:

| Active Ingredient | 5.0 |
| --- | --- |
| Polysorbate 80 | 2.0 |
| Sodium Chloride | 9.0 |
| Sodium carboxymethyl cellulose | 10.0 |
| Methyl paraben | 1.8 |
| Propyl paraben | 0.2 |
| Water, USP q.s. to 1 liter | |

The parabens, sodium chloride and carboxymethylcellulose are dissolved in one-half the total volume of water by heating to 95° C. to obtain a solution which is then filtered and autoclaved. The polysorbate is dissolved in one-third of the total volume of water, and the resulting solution also filtered and autoclaved. Sterile active ingredient is added to the second solution and the mixture passed through a sterile colloid mill to obtain a suspension of active ingredient. The first solution is added to the suspension with stirring then U.S.P. water added to 1 liter. Sterile vials are filled with the suspension while stirring.

Oral compositions also may be prepared from one of the above-named compounds as active ingredient in admixture with a pharmaceutically acceptable carrier. Suitable carriers for liquid compositions include water, glycols, oils, alcohols, flavoring agents, preservatives, coloring agents and the like; for solid preparations, starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed.

A representative composition is the following:

Oral Composition 5000 compressed tablets, each containing as active ingredient 100 milligrams of active ingredient are prepared from the following formulation:

| Active Ingredient | 500 |
|---|---|
| Starch | 700 |
| Dibasic calcium phosphate hydrous | 5000 |
| Calcium stearate | 25 |

The ingredients are finely powdered, mixed well, and then granulated with 10 percent starch paste. The granulation is dried and compressed into tablets using starch as a disintegrant and calcium stearate as lubricant.

TISSUE PREPARATION FOR ASSAY

The tissue is prepared by dissecting the uterus of estrogen-pretreated adult rats (0.3 mg/kg diethylstilbestral diproprionate, i.p., 24 hr) and placing in cold saline, then removing all fatty connective tissue, homogenizing in ice cold buffer #1 of 10 mM Tris HCl, 1.0 mM EDTA, 0.5 mM dithiothreitol, pH 7.4), centrifuging, resuspending the pellet in about 40 milliliters of ice cold buffer #2 of 50 mM Tris HCl, 5 mM MgCl$_2$, 0.1% BSA, pH 7.4), centrifuging and maintaining on ice. In the assay the pellet is resuspended to a final volume 1 gram original weight/24 ml ice cold buffer #2 and maintaining on ice for 10 minutes before assay.

What is claimed is:

1. A method for relaxing smooth muscle or reducing contractile activity by inhibiting oxytocin activity comprising administering to a patient an oxytocin inhibiting amount of a penicillide compound having the formula

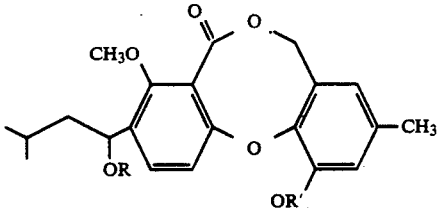

wherein R is H or —COCH$_3$ and R$^1$ is H, —COCH$_3$ or —CH$_3$, provided that if R$^1$ is methyl, R is COCH$_3$.

2. A method according to claim 1 wherein in the compound, R and R$^1$ are H.
3. A method according to claim 1 wherein in the compound R and R$^1$ are —COCH$_3$.
4. A method according to claim 1 wherein in the compound R is COCH$_3$ and R$^1$ is H.
5. A method according to claim 1 wherein in the compound R is COCH$_3$ and R$^1$ is CH$_3$.
6. A method for inhibiting premature labor comprising administering to a patient a therapeutic amount of a penicillide compound having the formula

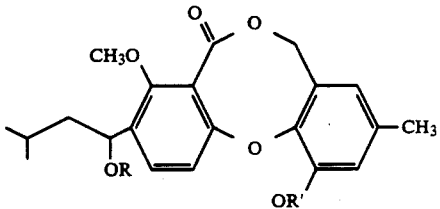

wherein R is H or —CHCH$_3$ and R$^1$ is H, —COCH$_3$ or CH$_3$, provided that if R$^1$ is methyl, is COCH$_3$.

* * * * *